(12) United States Patent
Warner et al.

(10) Patent No.: US 11,992,639 B2
(45) Date of Patent: May 28, 2024

(54) DEVICE FOR TARGETED DISPENSING OF NOURISHING MICROCAPSULES TO SKIN DURING SLEEP

(71) Applicant: Katya Warner, Bogota (CO)

(72) Inventors: Katya Warner, Bogota (CO); Diana Sotelo, Bogota (CO); Paula Peñaranda, Bogota (CO); Laura Daniela Sotelo Briceño, Bogota (CO); Johann Osma, Bogota (CO)

( * ) Notice: Subject to any disclaimer, the term of this patent is extended or adjusted under 35 U.S.C. 154(b) by 769 days.

(21) Appl. No.: 17/130,066

(22) Filed: Dec. 22, 2020

(65) Prior Publication Data

US 2021/0228851 A1  Jul. 29, 2021

Related U.S. Application Data

(63) Continuation-in-part of application No. 16/775,694, filed on Jan. 29, 2020, now Pat. No. 10,905,265.

(51) Int. Cl.
*A61M 35/00* (2006.01)
*A61K 8/11* (2006.01)
(Continued)

(52) U.S. Cl.
CPC .............. *A61M 35/00* (2013.01); *A61K 8/11* (2013.01); *A61K 8/66* (2013.01); *A61K 8/676* (2013.01);
(Continued)

(58) Field of Classification Search
CPC . A61M 35/00; A61M 2210/0606; A61K 8/11; A61K 8/66; A61K 8/676;
(Continued)

(56) References Cited

U.S. PATENT DOCUMENTS

| 233,934 | A | * | 11/1880 | Thompson | A01B 19/02 172/341 |
|---|---|---|---|---|---|
| 233,954 | A | | 11/1880 | Thompson | |
| 2,750,606 | A | * | 6/1956 | Freedlander | A47G 9/10 5/636 |
| 2,917,046 | A | * | 12/1959 | Fairbanks | A61M 15/00 D23/362 |

(Continued)

FOREIGN PATENT DOCUMENTS

| EP | 0955043 B1 | 11/1999 |
|---|---|---|
| EP | 1923423 A1 | 5/2008 |
| EP | 2731564 B1 | 5/2014 |

*Primary Examiner* — Fredrick C Conley
(74) *Attorney, Agent, or Firm* — Larson & Larson; Justin P. Miller; Frank Liebenow (57) ABSTRACT

The dispensing device allows for application of nourishing compounds, such as microcapsules, during rest. The elements of the dispensing device that contain the nourishing compounds are separable from the body of the device. Thus, the body of the device is washable without risk of washing away the desirable compounds. The device can take one of multiple embodiments. In the first embodiment, a lower layer forms the body of the device. The body is preferably formed from a compressible material, such as memory foam or other types of polyurethane foam. The upper layer includes a multiplicity of internal reservoirs that contain the nourishing compounds and/or microcapsules. When a user places her head on the device, the downward force created against the relevant storage body pushes the compounds/microcapsules out of the internal reservoir, exiting through the orifices and into the user's skin.

3 Claims, 7 Drawing Sheets

(51) Int. Cl.

| | | |
|---|---|---|
| | *A61K 8/66* | (2006.01) |
| | *A61K 8/67* | (2006.01) |
| | *A61K 8/73* | (2006.01) |
| | *A61K 8/92* | (2006.01) |
| | *A61Q 19/00* | (2006.01) |
| | *A61Q 19/08* | (2006.01) |
| | *A47G 9/00* | (2006.01) |
| | *A47G 9/02* | (2006.01) |

(52) U.S. Cl.
 CPC .............. *A61K 8/733* (2013.01); *A61K 8/922* (2013.01); *A61Q 19/00* (2013.01); *A61Q 19/08* (2013.01); *A47G 9/007* (2013.01); *A47G 9/0253* (2013.01); *A61K 2800/87* (2013.01); *A61M 2210/0606* (2013.01)

(58) Field of Classification Search
 CPC .... A61K 8/733; A61K 8/922; A61K 2800/87; A61Q 19/00; A47G 9/10
 See application file for complete search history.

(56) References Cited

U.S. PATENT DOCUMENTS

| | | |
|---|---|---|
| 4,882,220 A | 11/1989 | Ono et al. |
| 5,038,431 A | 8/1991 | Burgin et al. |
| 5,232,769 A | 8/1993 | Yamato et al. |
| 5,299,335 A | 4/1994 | Invester et al. |
| 6,574,809 B1 | 6/2003 | Rathbun |
| 6,805,263 B2 | 10/2004 | Garcia et al. |
| 6,997,355 B2 | 2/2006 | Duquet |
| 7,082,633 B1 | 8/2006 | Maarbjerg |
| 8,161,588 B1 | 4/2012 | Anson |
| 8,192,841 B2 | 6/2012 | Amundson et al. |
| 8,468,628 B1* | 6/2013 | Cheng .................. A47G 9/1054 5/652.2 |
| 9,220,275 B2 | 12/2015 | Chetboun |
| 9,408,419 B2 | 8/2016 | Almario et al. |
| 2004/0049854 A1* | 3/2004 | Schunk .................. A61L 15/44 5/652 |
| 2014/0271863 A1 | 9/2014 | Anderson et al. |
| 2017/0226668 A1 | 8/2017 | Kilickan et al. |
| 2018/0178183 A1* | 6/2018 | Berthier .................. A61K 8/737 |
| 2018/0280275 A1* | 10/2018 | Fevola .................. A61Q 19/00 |

* cited by examiner

DEVICE FOR TARGETED DISPENSING OF NOURISHING MICROCAPSULES TO SKIN DURING SLEEP

RELATED APPLICATIONS

This application is a continuation-in-part of U.S. application Ser. No. 16/775,694, filed Jan. 29, 2020, titled Device for targeted dispensing of nourishing microcapsules to skin during sleep.

FIELD

This invention relates to the field of skin nourishment and more particularly to a device for focused and target dispensing of microcapsules.

BACKGROUND

The health of the skin is contingent on the presence of the appropriate nutrients. Nutrients promote cell renewal, prevent skin aging, as well as being a precursor to collagen formation, create skin firmness, elasticity, and luminosity. These nutrients are assimilated by the body to improve the functioning of the organs, including the skin. But the body's ability to assimilate these nutrients notably decreases as one ages, creating health and aesthetic complications.

Nutrients are naturally present in different food sources, as well as synthetically as supplements. The amount of nutrients provided by food varies greatly according to the type of food consumed, therefore, the synthetic intake of nutrients has become the most viable option to avoid a deficiency of these and as a consequence of this an aesthetic affectation.

Therefore, it is considered important to develop a device capable of quickly and efficiently providing this type of nutrients to the body, without requiring the user to remember to take pills, sit through long aesthetic treatment.

What is needed is a device that will allow a user to easily apply nourishing compounds to the skin for extended periods of time, allowing the user to fully realize the beneficial effects.

SUMMARY

The dispensing device allows for application of nourishing compounds, encapsulated in microcapsules, during rest.

The elements of the dispensing device that contain the encapsulated nutritional compounds are separable and removable from the body of the device. Thus, the body of the device, and any associated cover, such as a pillowcase, is washable without risk of washing away the desirable compounds.

The device can take one of multiple embodiments.

In the first embodiment, a lower layer forms the body of the device. The body is preferably formed from a compressible material, such as memory foam or other types of polyurethane foam. Natural materials are also anticipated, such as wool, cotton, down, latex, and similar materials.

The upper layer, or top layer, includes a multiplicity of discrete, internal reservoirs that contain the nourishing compounds and/or microcapsules.

When a user places her head on the device, the downward force created against the relevant storage body/internal reservoir pushes the compounds/microcapsules out of the internal reservoir, exiting through the orifices and into the user's skin.

The internal reservoirs may be located at the desired areas, for example, at the cheek and neck, and only activated by direct pressure.

Alternatively, the reservoirs may be placed at remote locations, but activated by pressure against a central reservoir by the weight of the head.

Regardless of the chosen methodology, if microcapsules are used, the presence of a gas, preferably air, within the internal reservoirs is required.

The air may be introduced into the reservoirs by the deflation/inflation action of the reservoir/pouch as force is applied and released.

Or a mechanical device can introduce air, such as a pump. The pump can be a bellows that is actuated by weight of the user's head. Each reservoir can have its own bellows, or a single bellows can supply air to multiple reservoirs.

Optionally, the motive force for dispensing the micro capsules is created by a powered source, such as a fan. The fan is preferably electrical. The use of an electrical device allows for control of the dispensing speed without depending on the weight of the user's head. Additionally, other features, such as a timer, can be incorporated to control when compounds, or microcapsules, are dispensed.

Microcapsules are the combination of a small particle or droplet and a surrounding coating. Microencapsulation can enclose solids, liquids, or gases inside a thin wall referred to as a film or membrane. The film protects the contents, preventing degradation and changing the physical properties of the resulting substance by separating the liquid from the environment. Thus, the feel of the resulting microcapsules is different, and interactions are changed by, for, example, protecting the contents from oxygen.

The material inside the microcapsule is referred to as the core, internal phase, or fill, with the wall referred to as a shell, coating, or membrane.

Within the membrane are substances such as anti-oxidants, sunscreen, vitamins, retinoids, peptides, or other substances that nourish the skin.

Alternatively, or in addition, the substances can include compounds and chemicals for medical treatments, specifically compounds absorbed through the skin.

Specific embodiments were produced and tested. The embodiments are described herein.

First Embodiment

In this embodiment, the procedure is described as used to produce microcapsules that encapsulate different substances.

The manufacture of microcapsules is based on the flow-focusing method, using a water-soluble biopolymer solution, an oil phase, and a salt, inside a flow-focusing microfluidic device. Sodium alginate at concentrations ranging from 0.5 to 1.5% weight/volume (wt./vol.), dissolved in water, was used as the biopolymer solution. Commercial vegetable oil, specifically soy and palm, was used as the oil phase. Copper sulfate at concentrations from 2.0 to 5.0% wt./vol. was used as the salt. A microfluidic device made of Polymethylmethacrylate (PMMA) was used to produce the flow-focusing. Oil phase and the biopolymer solution were independently pumped into the microfluidic device. Image observation was taken using optical microscopes. After the capsules were formed within the device, they were cross-linked in the salt solution for approximately 1 to 8 hours. Finally, the capsules were filtered using filter paper and a funnel and stored at room temperature until later use.

Microcapsules ranging from 200 to 1200 μm in diameter were obtained by this method.

Second Embodiment

In this embodiment, the procedure to produce microcapsules that contained natural dyes and pigments compatible with skin products is described.

The manufacture of microcapsules is based on the method described in the first embodiment, by previously mixing the dye components to the biopolymer solution prior to its entrance into the microfluidic device. As model pigments, Ultramarine Blue dye (CI 77007) or Red Oxide (CI 77491) at concentrations from 0.25 to 0.75% volume/volume (vol./vol.) was mixed to a 0.5 to 1.5% wt./vol. sodium alginate solution. The procedure was followed exactly as described in the first embodiment. The produced microcapsules contained the dyes and pigments, identifiable by the color of the microcapsules.

Third Embodiment

In this embodiment, the procedure to produce microcapsules that contained vitamins is described.

The manufacture of microcapsules is based on the method described in the first embodiment, by previously mixing the vitamin product to the biopolymer solution prior to its entrance into the microfluidic device. As model vitamin, ascorbic acid, also known as vitamin C, at a concentration from 0.25 to 0.75% v/v was mixed to a 0.5 to 1.5% w/v sodium alginate solution. The following procedure was exactly as described in the first embodiment.

Fourth Embodiment

In this embodiment, the procedure to produce microcapsules that contained proteins is described.

The manufacture of microcapsules is based on the method described in the first embodiment, by previously mixing the protein to the biopolymer solution prior to its entrance into the microfluidic device. As model protein, laccase enzyme (EC 1.10.3.2) with an activity of 2800 U/L, was mixed to a 0.5 to 1.5% w/v sodium alginate solution. The following procedure was exactly as described in the first embodiment. To determine the presence of the protein inside the microcapsules, laccase was previously labelled with Rhodamine B to identify its presence via fluorescence as shown in FIG. 13F.

Fifth Embodiment

In this embodiment, the procedure to incorporate microcapsules in a pillow and recreates the release phenomena is described.

Produced microcapsules, as described in the second embodiment, were used to study the release phenomena. A cellulose-based textile device, used as a model pillow made of natural cellulosic fibers, was filled with the microcapsules in internal reservoirs. A simulated head was built using a 660 g bag and a heated textile at 35° C. to recreate the pressure and temperature produced by the head on the pillow. The phenomenon was monitored during one hour by optical photography. The interaction of the 660 g bag with device, triggered the microcapsules to be expelled through the orifices of the device, and the constant pressure and temperature showed the release of the encapsulated substance through time into the simulated head.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
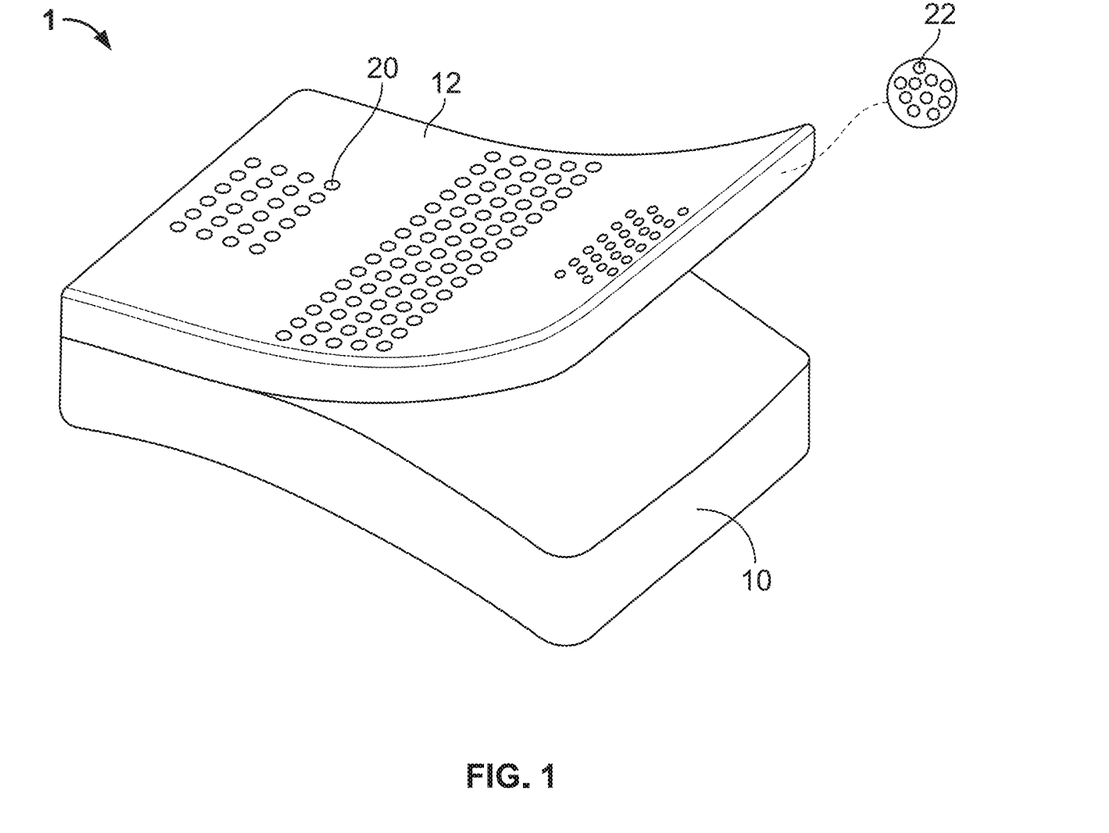
FIG. 1 illustrates an isometric view of a first embodiment of the dispensing device.

Referring to FIG. 1, an isometric view of a first embodiment of the dispensing device is shown.

The dispensing device 1 is shown formed from a body 10 supporting a dispensing layer 12. The dispensing layer 12 forms the entire top of the dispensing device 1, and includes a multiplicity of orifices 20 out of which microcapsules 22 may pass.

Figure 2:
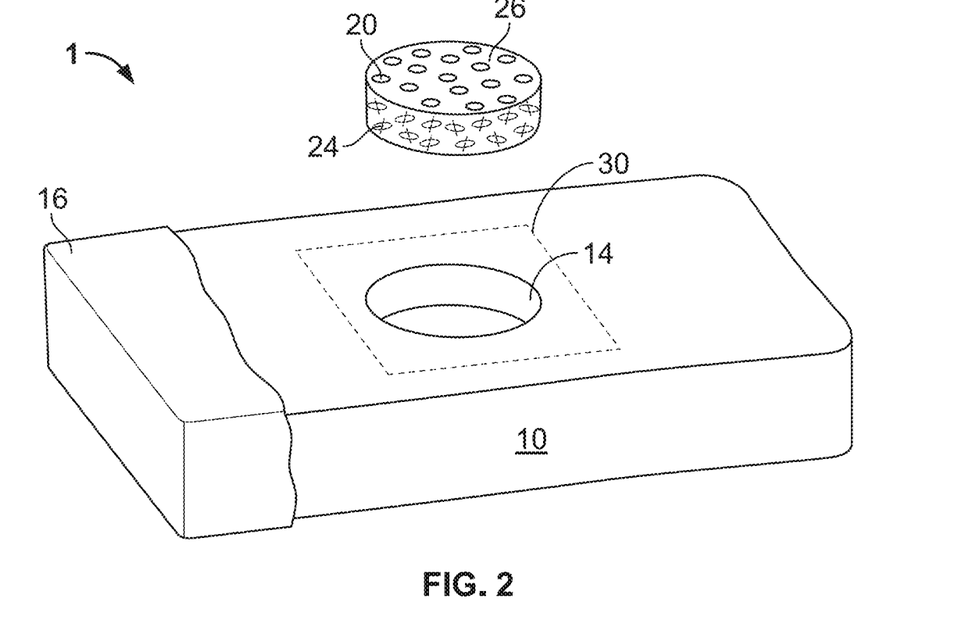
FIG. 2 illustrates an isometric view of a second embodiment of the dispensing device.

Referring to FIG. 2, an isometric view of a second embodiment of the dispensing device is shown.

The dispensing device 1 again includes a body 10, but in this embodiment includes a recess 14 into which a storage body 26 is placed. The storage body 26 includes internal reservoirs 24 inside of which are held microcapsules 22 (see FIG. 1), which exit through orifices 20.

The embodiment shown in FIG. 2 is a pillow, including a covering 16 or pillowcase.

Figure 12:
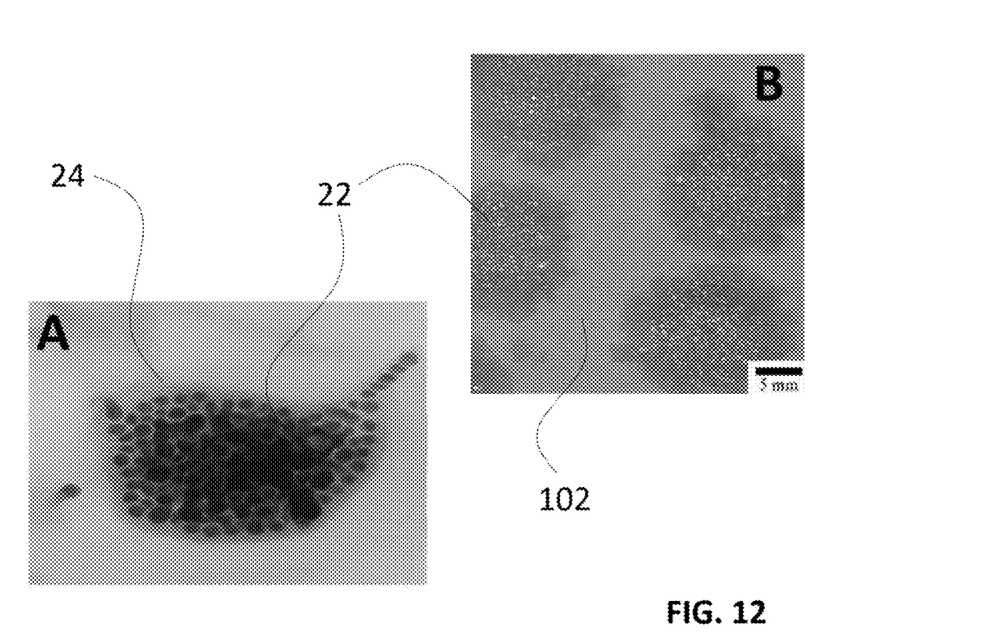
FIG. 12 illustrate microcapsules inside a reservoir, and as applied to a simulated head.

The location of the recess 14 places the orifices 20 in a head and neck zone 30, thus providing microcapsules 22 (see FIGS. 1 and 12) to the head and neck of a user.

Figure 3:
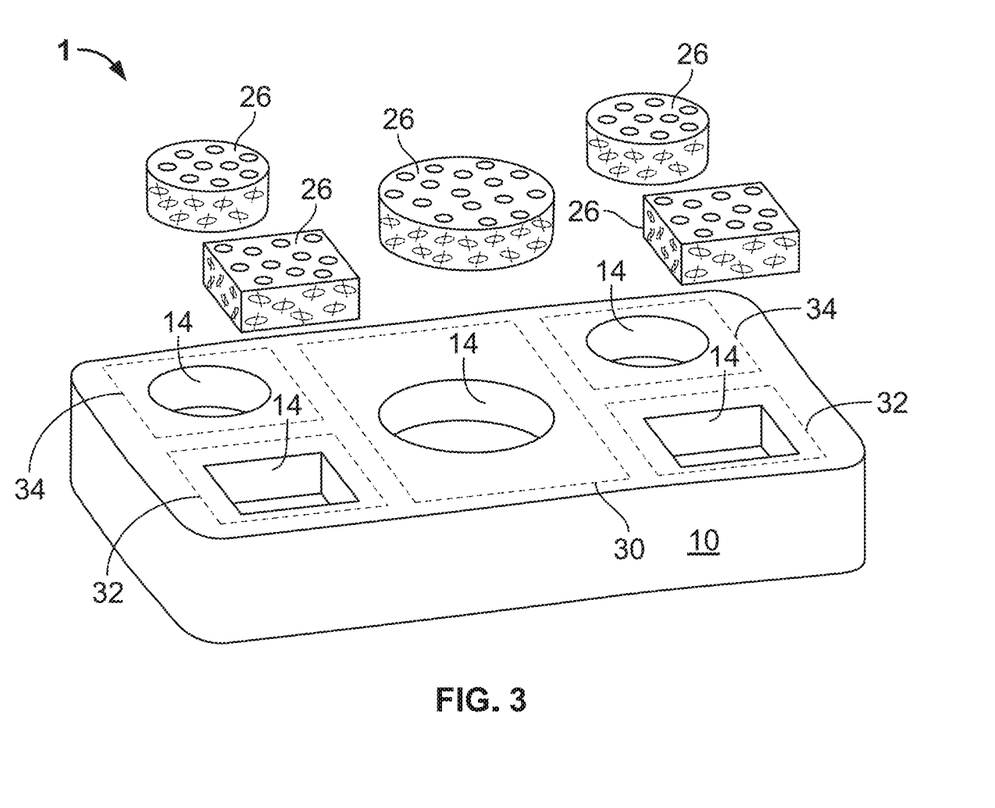
FIG. 3 illustrates an isometric view of a third embodiment of the dispensing device.

Referring to FIG. 3, an isometric view of a third embodiment of the dispensing device is shown.

In this embodiment, there are multiple recesses 14 into which storage bodies 26 are placed.

The result is storage bodies 26 directed to different parts of the user's head. The central storage body 26 is in a head and neck zone 30, with the adjacent storage bodies 26 forming a cheek zone 32 and forehead zone 34, with contact made when a user rolls her head to one side or the other.

Figure 4:
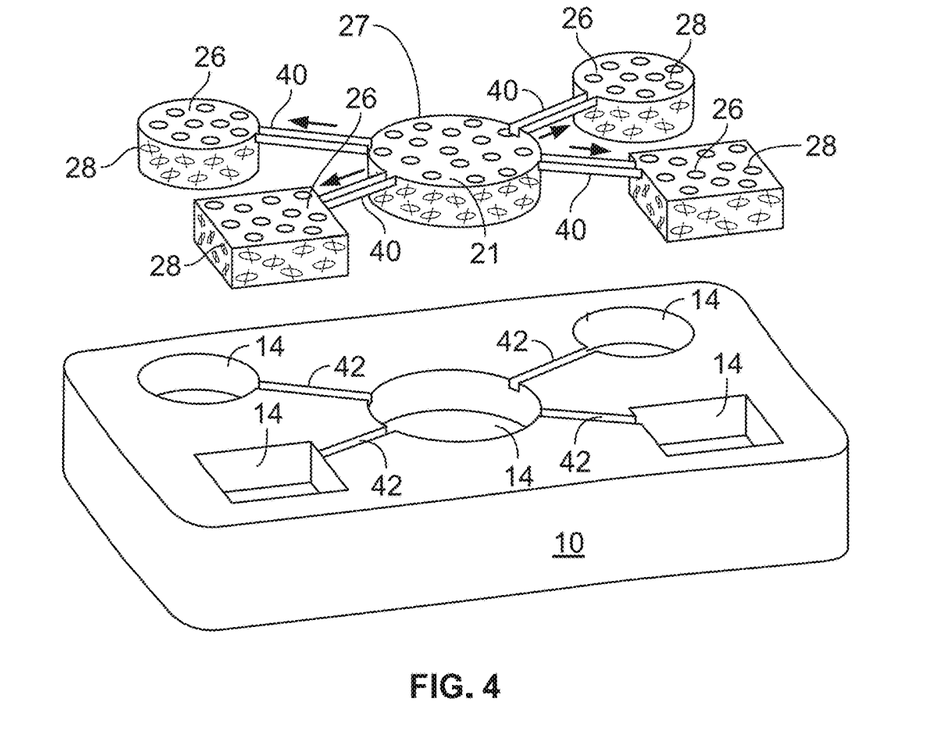
FIG. 4 illustrates an isometric view of a fourth embodiment of the dispensing device.

Referring to FIG. 4, an isometric view of a fourth embodiment of the dispensing device is shown.

In this embodiment, the recesses 14 are connected by branch recesses 42. The storage bodies 26 are divided into a central pouch 27 and multiple remote pouches 28. The central pouch 27 is initially charged or filled with nourishing compounds or microcapsules 22 (see FIG. 1), which are pushed from the central pouch 27 to the remote pouches 28 by the weight of the user's head.

Figure 5:
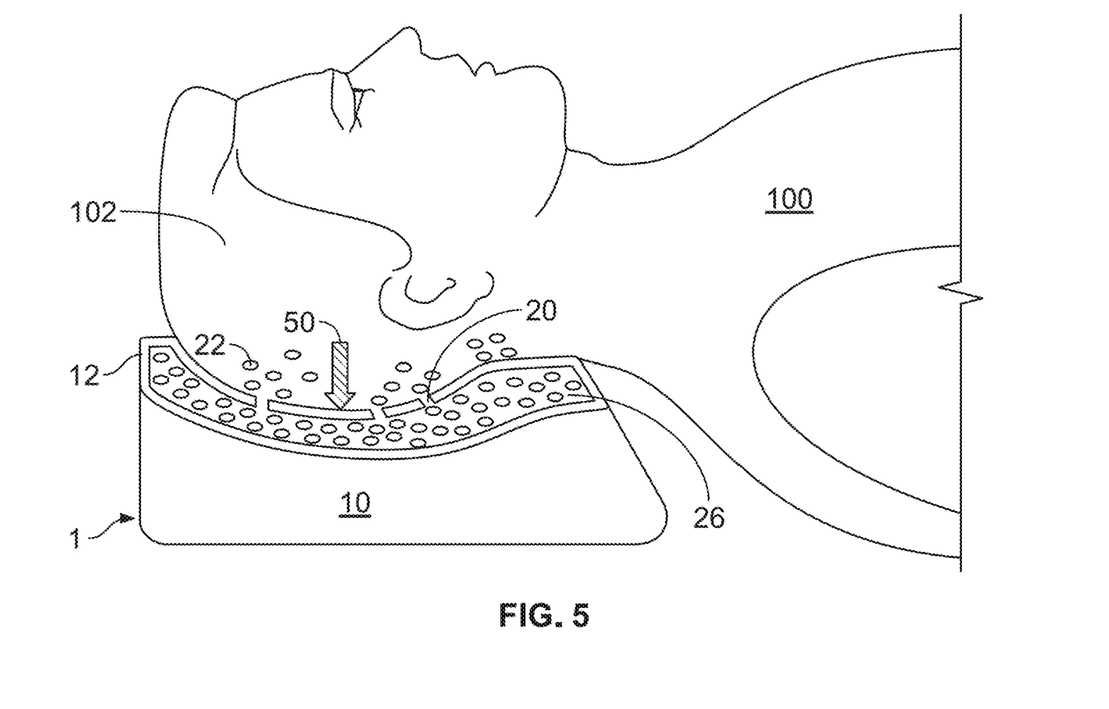
FIG. 5 illustrates a side cross-sectional view of an embodiment of the dispensing device.

Referring to FIG. 5, a side cross-sectional view of an embodiment of the dispensing device is shown.

The user 100 places his head 102 on the dispensing device 1, creating a force 50. Microcapsules 22 are pushed out of the reservoir 26 of the dispensing layer 12, through the orifices 20 and onto the user's head 102.

Figure 6:
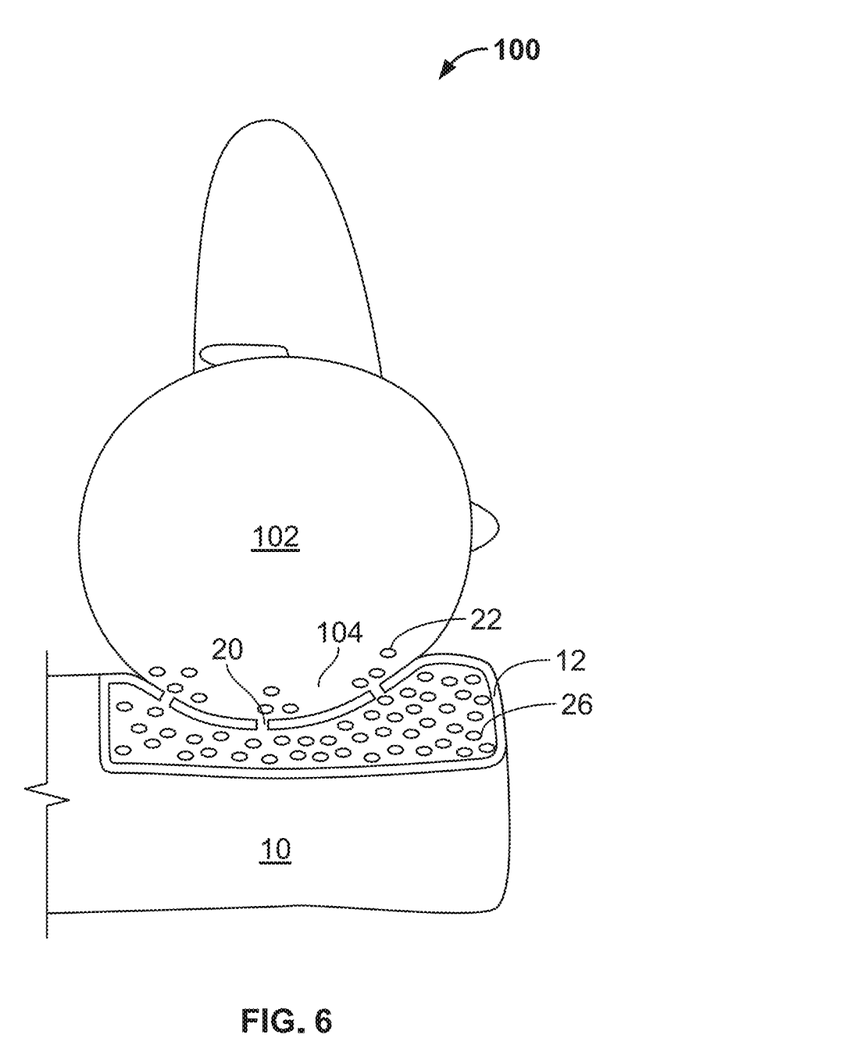
FIG. 6 illustrates a top cross-sectional view of an embodiment of the dispensing device.

Referring to FIG. 6, a top cross-sectional view of an embodiment of the dispensing device is shown.

The user 100 has now rolled on his side, placing his cheek 104 of his head 102 on the dispensing device 1. Again, microcapsules 22 are pushed out of the reservoir 26 of the dispensing layer 12, through the orifices 20 and onto the user's head 102.

Figure 7:
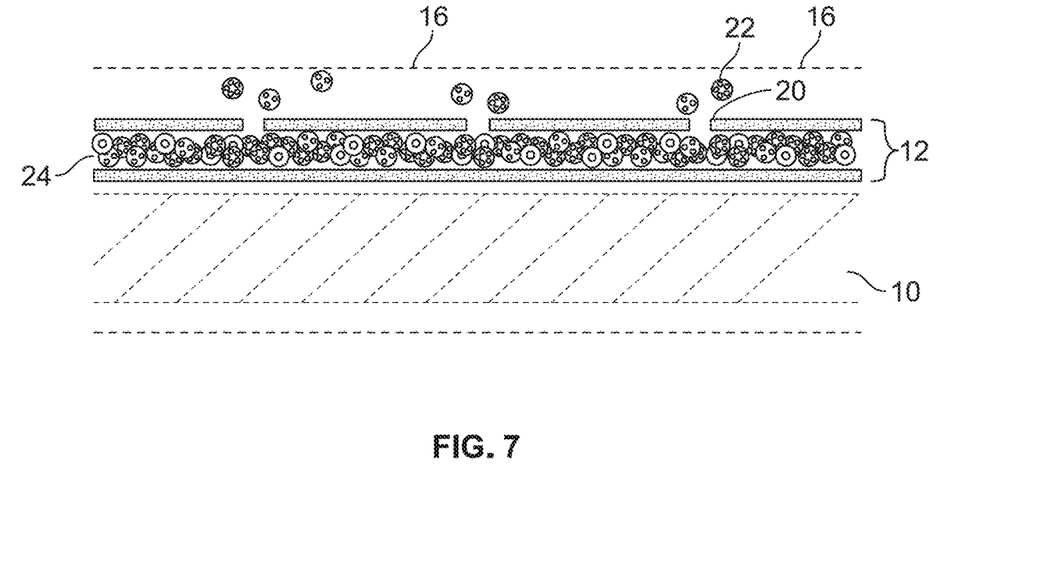
FIG. 7 illustrates a detail view of an embodiment of the dispensing device is shown.
Figure 8:
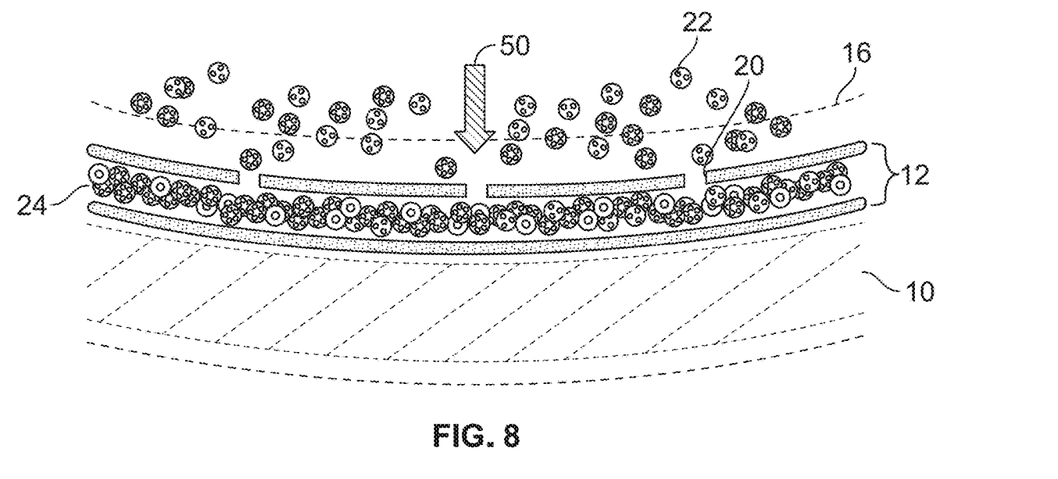
FIG. 8 illustrates a detail view of an embodiment of the dispensing device after a force is applied is shown.

Referring to FIGS. 7 and 8, detailed views of an embodiment of the dispensing device are shown.

The body 10 supports a dispensing layer 12, with a covering 16 above.

Microcapsules are held within the internal reservoir 24. When a force 50 is applied, such as from a user's head, the microcapsules 22 are forced out of the orifices 22, and through the covering 16.

Figure 9:
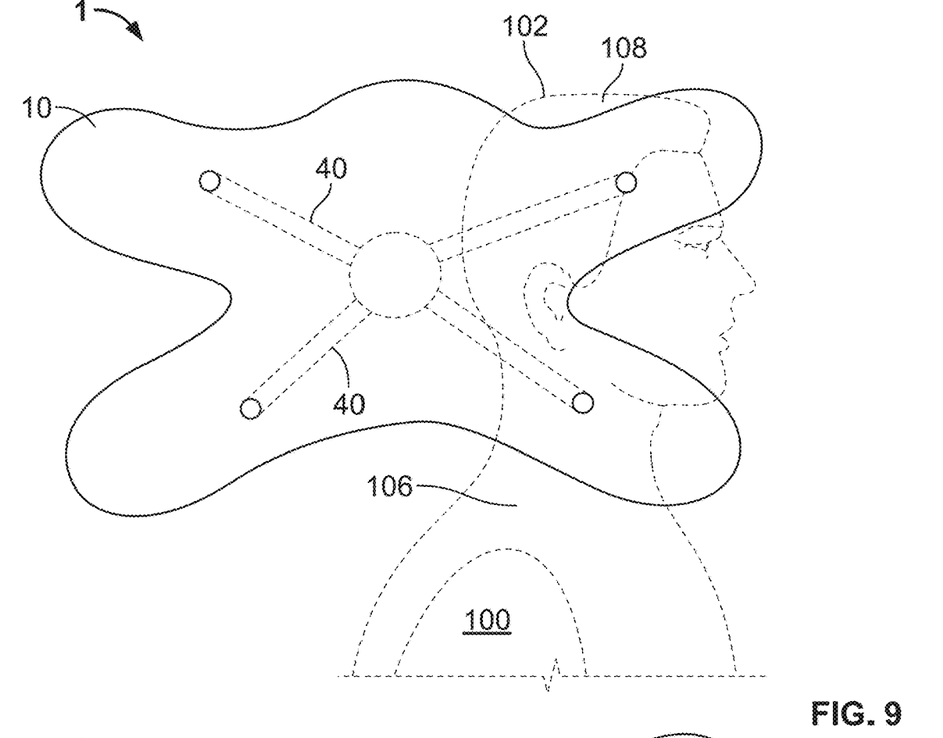
FIG. 9 illustrates an embodiment of the dispensing device with extensions to reduce pressure on the skin around the eyes and mouth.
Figure 10:
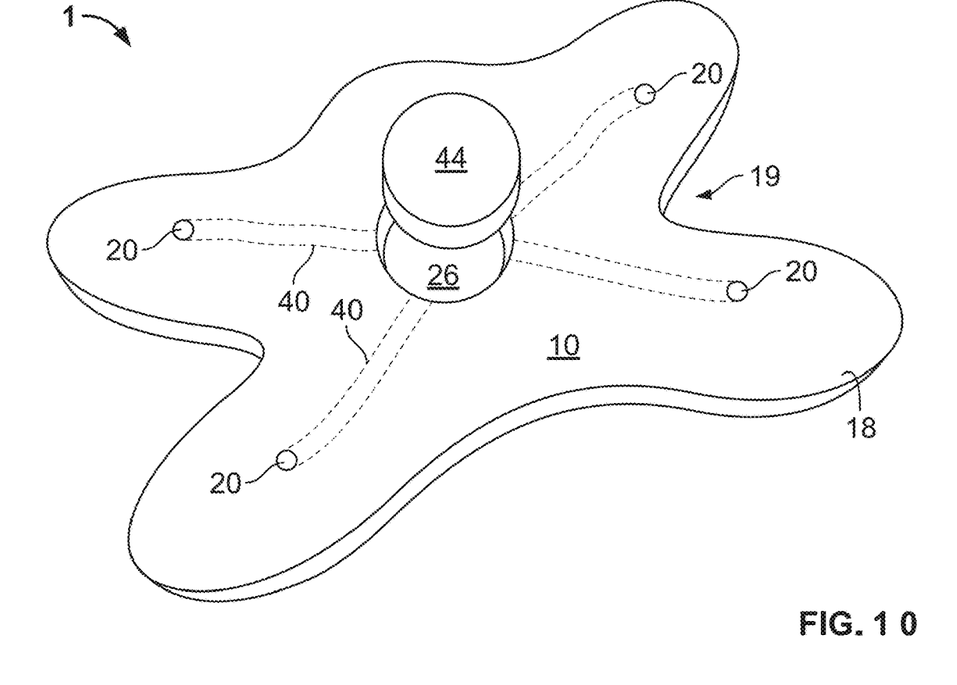
FIG. 10 illustrates a second view of an embodiment of the dispensing device with extensions to reduce pressure on the skin around the eyes and mouth.

Referring to FIGS. 9 and 10, an embodiment of the dispensing device with extensions to reduce pressure on the skin around the eyes and mouth is shown.

The dispensing device 1 is shown with body 10 include extensions 18. Between the extensions 18 are gaps 19. When in use, the user 100 places his head 102 on the extensions 18, causing the mechanical dispenser 44 to press against the storage body 26, causing the discharge of microcapsules through the branches 40 to the orifices 20. The microcapsules exit at the neck 106 and hair 108 of the user 100.

The gap 19 is placed such that pressure is reduced against the skin around the eyes and mouth of the user 100, thus preventing unnecessary stretching of the associated skin.

Figure 11:
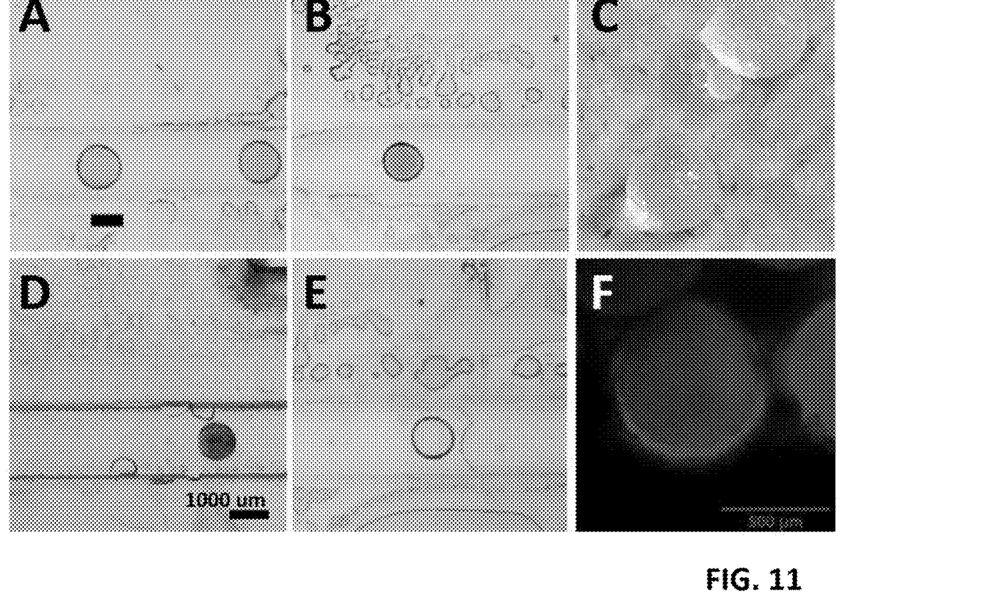
FIG. 11 illustrates microcapsules containing dyes and pigments, vitamins and proteins.

Referring to FIG. 11, microcapsules containing dyes and pigments, vitamins and proteins, were produced to test the device. The presence of the encapsulated substances inside of the microcapsules was verified via the presence of color or by fluorescence.

Referring to FIG. 12A, microcapsules 22 are stored inside an internal reservoir 24. In FIG. 12B, the encapsulated substance and microcapsules 22 are released on a simulated head 102.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A compressible device with integrated microcapsule reservoirs, the device comprising:
   a body;
   a discrete and removable reservoir for storage of microcapsules, the discrete and removable reservoir surrounded by the body and removeable from the body;
   the microcapsules formed from:
      a water-soluble biopolymer solution;
      an oil;
      and a salt;
      whereby the microcapsules are a membrane surrounding a skin-nourishing chemical;
   a second reservoir;
   the discrete and removable reservoir and second reservoir connected by a branch;
   the branch carrying microcapsules from the reservoir to the second reservoir when a force is applied to the reservoir; and
   an actuation mechanism for discharge of the microcapsules through orifices present in the reservoirs.

2. The device of claim 1 wherein the water-soluble biopolymer solution further comprises ascorbic acid.

3. The device of claim 1, wherein the body further comprises:
   a recess;
      the discrete and removable reservoir sitting within the recess.

* * * * *